United States Patent [19]

Stetter et al.

[11] Patent Number: 4,795,543

[45] Date of Patent: Jan. 3, 1989

[54] SPIN COATING OF ELECTROLYTES

[75] Inventors: Joseph R. Stetter, Naperville; G. Jordan Maclay, Maywood, both of Ill.

[73] Assignee: Transducer Research, Inc., Naperville, Ill.

[21] Appl. No.: 53,722

[22] Filed: May 26, 1987

[51] Int. Cl.⁴ .............................................. G01N 27/30
[52] U.S. Cl. .................... 204/412; 29/570.1; 204/425; 427/240
[58] Field of Search ................ 427/240; 204/415, 425, 204/412; 29/592 R

[56] References Cited

U.S. PATENT DOCUMENTS

| 4,068,019 | 1/1978 | Boeckl | 427/82 |
| 4,124,411 | 11/1978 | Meuleman et al. | 136/89 |
| 4,267,212 | 5/1981 | Sakawaki | 427/240 |

FOREIGN PATENT DOCUMENTS

| 7136053R | 10/1971 | Japan | 427/240 |
| 7142658R | 12/1971 | Japan | 427/240 |

OTHER PUBLICATIONS

IBM Technical Disclosure Bulletin; vol. 19, No. 3 (Aug. 1976) "Method of Depositing Pastes and Slurries", B. J. Foster and B. Narken, p. 857.

IBM Technical Disclosure Bulletin; vol. 18, No. 2 (Jul. 1975) "Striation-Free Resist Coating Process", E. R. Mondou and P. R. Schmidt, pp. 391-392.

IBM Technical Disclosure Bulletin; vol. 16, No. 5 (Oct. 1973) "Spin Coating Photoresist", P. W. Reed and L. R. Weaver, pp. 1535-1536.

Primary Examiner—G. L. Kaplan
Attorney, Agent, or Firm—Larson & Taylor

[57] ABSTRACT

Methods for spin coating electrolytic materials onto substrates are disclosed. More particularly, methods for depositing solid coatings of ion-conducting material onto planar substrates and onto electrodes are disclosed. These spin coating methods are employed to fabricate electrochemical sensors for use in measuring, detecting and quantifying gases and liquids.

26 Claims, 3 Drawing Sheets

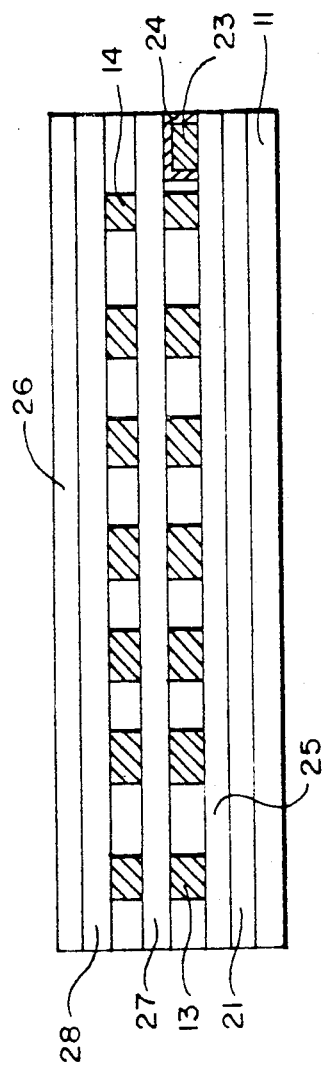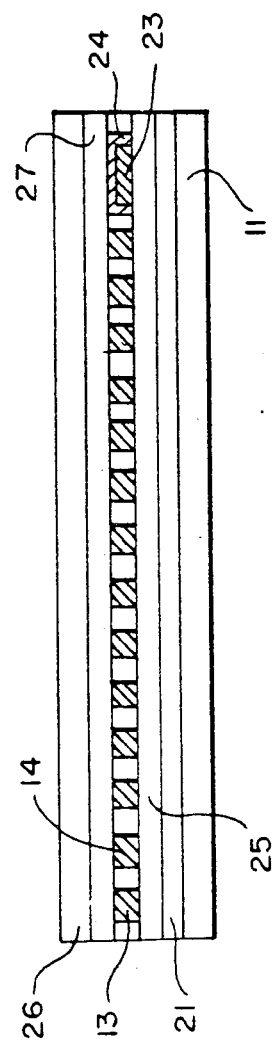
FIG. 4
FIG. 3

SPIN COATING OF ELECTROLYTES

This invention was made with Government support under contract number ANL-61892401 awarded by the Department of Energy. The Government has certain rights in this invention.

FIELD OF THE INVENTION

The invention relates to methods for spin coating electrolytic materials onto a substrate. More specifically the invention relates to improved methods for forming solid coatings of electrolytes on planar substrates as well as on electrodes.

BACKGROUND OF THE INVENTION

Electrochemical sensors for analyzing gases have existed for quite some time. Such sensors include the Clark Cell described in U.S. Pat. No. 2,913,386 issued Nov. 17, 1959, and the Ross-type Cell described in U.S. Pat. No. 3,260,656 issued on July 12, 1966 to James W. Ross, Jr. These apparatus employ liquid electrolytes. The use of liquid electrolytes necessitates a chamber or holding means for confining the liquid electrolyte in the electrochemical sensor. As a result, these electrochemical sensors are often large and bulky and suffer from other disadvantages that can include slow response times and variations in sensor readings due to stresses applied to the electrodes caused by temperature and/or pressure variations.

An attempt at solving some of these problems is described in U.S. Pat. No. 4,076,596 issued to Connery et al. on Feb. 28, 1978. This patent discloses an electrolytic cell for measuring the concentration of a species in a fluid material. The electrolytic cell is constructed by depositing closely spaced, interleaved inert electrode surfaces on the surface of an insulating substrate and covering the electrode surfaces with a thin film of solid electrolyte and a permeable membrane. The Connery et al. apparatus is a completely self-contained electrochemical sensor which requires no liquid electrolytic solution to function. This type of sensor is quite desirable because it minimizes the problems associated with slow response times and bulky sensors.

However, several problems were discovered during the fabrication of the Connery et al. type apparatus. For instance, the electrolyte coating had a tendency to peel off of the substrate. Moreover, application of electrolyte coatings over electrodes as in Connery et al. often results in holes, dimples or warps in the structure of the electrolyte coating at the edges of the electrodes. These structural defects in the electrolyte film are probably due to poor step coverage at the electrode edge by the electrolyte coating and these defects could cause short circuits or other defects in the structure that cause poor operating specifications. The electrolyte coatings also exhibit a tendency to tear near the edges of the electrodes during the coating processes. This tearing adversely affects the properties of the sensor. Another problem that is typically encountered as a result of coating a solid electrolyte layer over electrodes is that stresses due to temperature, humidity and/or pressure often distort the electrolyte layer and thereby adversely affect the properties of the sensor. Finally, coating the electrolyte layer over the uneven surface of the electrodes often results in inconsistent electrolyte coating thicknesses and hence, inconsistent sensors.

Accordingly, it is the primary object of the present invention to provide a process for spin coating electrolytes which overcomes the disadvantages of the prior art.

It is a further object of the present invention to provide a process for spin coating a solid electrolyte layer onto the surface of a substrate to obtain thin, smooth and consistent electrolyte coatings under which electrodes may be located.

It is a still further object of the present invention to provide methods of coating a solid electrolyte layer on the surface of previously deposited electrodes which results in smooth and consistent coatings of electrolyte.

It is a still further object of the present invention to provide a method for making planar electrochemical sensors which are completely self-contained and include a solid electrolyte.

It is a still further object of the present invention to provide a method for making sandwich-type electrochemical sensors which incorporate several layers of solid electrolytic material.

It is a still further object of the present invention to provide methods of making electrochemical sensors having increased resistance to stresses caused by temperature, humidity and pressure.

These and other objects of the present invention will be apparent to one of ordinary skill in the art from the summary of detailed description which follow.

SUMMARY OF THE INVENTION

The present invention relates to a method for the production of a structurally stable, solid electrolyte for use in the fabrication of electrochemical sensors comprising the step of spin coating an electrolytic material onto the surface of an insulating substrate, said electrolytic material being of sufficient viscosity to provide a uniform coating of a solid, structurally stable electrolyte layer on said substrate.

Another embodiment of the present invention relates to a method for the production of an electrochemical sensor comprising the steps of spin coating an electrolytic material onto the surface of an insulating substrate, said electrolytic material being of sufficient viscosity to provide a uniform coating of a solid, structurally stable electrolyte layer on said substrate, depositing a working electrode and at least one other electrode onto said layer of electrolytic material, and connecting an electrical power source to said working electrode and at least one another electrode to thereby complete a circuit in which current is capable of flowing through both of said electrodes as a result of at least one electrochemical reaction occuring at said working electrode.

Yet another embodiment of the present invention relates to a method for the production of a sandwich-type electrochemical sensor comprising the steps of spin coating an electrolytic material onto the surface of an insulating substrate, said electrolytic material being of sufficient viscosity to provide a uniform coating of a solid, structurally stable first electrolyte layer on said substrate, depositing at least one electrode onto said first layer of electrolytic material, spin coating an electrolytic material onto said at least one electrode, said electrolytic material being of sufficient viscosity to provide a uniform coating of a solid, structurally stable second electrolytic layer on said at least one electrode, depositing a working electrode onto said layer of electrolytic material, and connecting an electrical power source to said working electrode and to at least one other electrode to thereby complete a circuit in which current is capable of flowing through both of said electrodes as a result of at least one electrochemical reaction occurring at said working electrode.

BRIEF DESCRIPTION OF THE DRAWINGS

FIG. 3 is a cross-sectional view of an alternate embodiment of the amperometric electrochemical sensing apparatus of the present invention.

FIG. 4 is a cross-sectional view of a sandwich-type amperometric electrochemical sensing apparatus in accordance with the present invention.

DETAILED DESCRIPTION OF THE PREFERRED EMBODIMENTS

Figure 1:
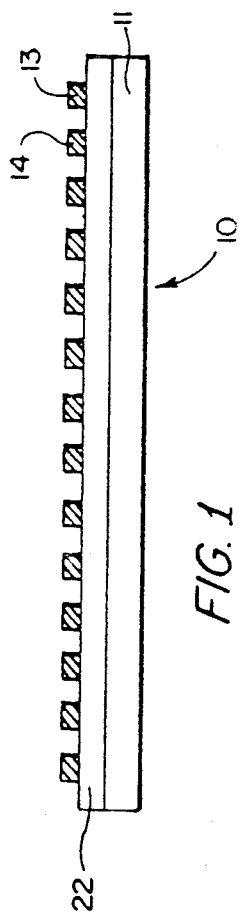
FIG. 1 is a cross-sectional view of the amperometric electrochemical apparatus of the present invention.

The invention relates to the use of a spin coating process to coat an electrolytic material onto a substrate. In general, spin coating processes employ a nozzle for feeding the coating material to the substrate, and a turntable powered by a motor. The substrate to be coated is placed onto the turntable and the turntable is rotated to rotate the substrate. Coating is accomplished by rotating the substrate while providing a liquid coating material through the nozzle to the surface of the substrate. The liquid coating material will spread outwardly on the substrate as a result of rotational forces. As a result, the coating material wets the surface of the substrate and forms a smooth, even coating thereon.

One of the primary goals of the present invention is to use spin coating processes to coat electrolytes onto insulating substrates as well as onto electrode surfaces. Certain problems are encountered when one attempts to spin coat electrolytes onto insulating or noninsulating substrates. For instance, the electrolytic material will often peel off the substrate after it dries. In addition, strains often develop in the electrolytic film between wet and dry areas as the film wets thereby resulting in uneven coatings having inconsistent properties.

Another goal of the present invention is to provide solid electrolytic materials having good structural stability and excellent resistance to thermal and physical stresses which are generally homogeneous. This is an improvement over the prior art because sheet electrolyte structures, such as perfluoro linear polymers, make a poor substrate for deposition of electrodes. Commercially available films, such as Nafion 117 sheet (i.e., Du Pont, Wilmington, Del.), have been found unsuitable for use as solid electrolytes because they are poor substrates for the deposition of electrodes. The Nafion sheets do not adhere well to the electrode and gold electrodes can be cleanly removed from the Nafion substrate using the scotch tape test. In addition, when the film with electrodes deposited therein is wet with water, cracks appear. Further, the Nafion sheet tends to swell upon exposure to moisture and flexes during handling due to insufficient structural stability. This swelling and flexing causes additional cracking and abrading of the electrodes deposited on the surface. As a result, it was concluded that electrode deposition on Nafion sheet forms electrodes which undergo significant changes in the mechanical and electrical properties during wetting and subsequent use and can cause unwanted and perhaps catastrophic changes in a sensor's analytical characteristics.

As a result, there is a need for improved solid materials for use as electrolytes in electrode structures. The method of the present invention provides such a structure by spin coating at least one suitable ion exchange membrane onto the surface of a substrate. Such ion exchange membranes include perfluoro linear polymers like Nafion (available from Du Pont), polysulfonic acids including polystyrene sulfonic acid, slurries including ion exchange materials, wicks or other suitable materials and ion exchange membranes incorporating fibrous or binder materials for adding strength to the ion exchange membrane.

In order to obtain a solid electrolyte layer having the requisite thickness and structural properties, the viscosity of the electrolytic material must be from about 30 to about 400 centistokes. Increases in the viscosity will cause a corresponding increase in the film thickness of the coated electrolyte on the substrate, at a given spin velocity. The increases in the film's thickness, in turn, result in a more structurally stable electrolyte having increased mechanical strength. However, increased thickness of the electrolytic layer may also decrease the electrolytic resistance of the system. Conversely, a thick electrolyte may slow diffusion processes and lead to a slower response. Thus, the film thickness should be chosen such that the optimum sensor specifications for a particular application are achieved.

Another important feature of the present invention is the use of a spinner to coat the electrolyte onto the substrate. During spin coating the substrate must be rotated at a speed of about 50 r.p.m. to about 5000 r.p.m. More preferably, the spin speed of the substrate will be between 300 r.p.m. and 700 r.p.m. and, most preferably, be from about 500 r.p.m. to about 650 r.p.m. These spin speeds provide thin uniform coatings of the electrolyte material on the substrate for typical materials used in these examples. Adjustment of the spin speed in combination with adjustments of the viscosity of the electrolytic solution being coated onto the substrate will provide the desired properties of the solid electrolytic layer.

Suitable substrates for use in the present invention include insulating substrates. Such insulating substrates may include, but are not limited to, silicon, ceramic, or a magnetic substrate such as oxides of iron. Other possible substrates include sapphire, glass, alumina and polymers. The substrates must be suitably prepared for the spin coating process. This preparation may include cleaning and lapping in a manner sufficient for adhesion and smoothness of the spin coated film.

A thin, hydrophilic coating on the surface of the substrate also aids in adhering the substrate to the electrolyte layer when the electrolyte layer is polar (e.g., aqueous or alcoholic). The major criterion is that the electrolyte or electrolyte solution should wet the substrate to some extent. Therefore, it is preferred to coat the surface of the substrate with a thin coating of a hydrophilic material. The most preferred hydrophilic materials for this purpose are oxides. Alternatively, the surface of the substrate may be oxidized to form the oxide coating rather than coating the surface with a separate layer of oxide. An example of a suitable oxide is silicon dioxide which may be formed by simple oxidation of the surface of the silicon substrate.

Another method of promoting adhesion of the electrolyte to the substrate involves the use of adhesion promoters. For example, adhesion promoters such as N-(trimethoxysilylpropyl)-N,N,N-trimethyl-ammonium chloride, octadecyltrichlorosilane, and 8-hydroxy-1,3,6-pyrenetrisulfonic acid trisodium salt may be used to promote adherence of perfluoro linear polymers to siliceous substrates. These adhesion promoters add additional strength to the electrolyte-substrate bond by chemically bonding the electrolyte to the substrate. The adhesion promoters are applied to the substrate just prior to the spin coating of the electrolyte onto the substrate. Such promoters are described in Szentirmay, M. N., Campbell, L. F., and Martin, C. R., *Silane Couplng Agents for Attaching Nafion to Glass and Silica*, Anal. Chem., Vol. 58, pp. 661-662, March 1986, which is hereby incorporated by reference.

Once the electrolytic layer has been deposited onto the hydrophilic surface of the substrate, it is desirable to deposit at least one electrode onto the surface of the electrolytic layer. The electrodes which may be used in the present invention are preferably metal electrodes. These electrodes may be deposited on the surface of the electrolytic medium through the use of thick film, or thin film techniques. Such methods include sputtering and/or evaporation onto the electrolytic surface of a thin film of metal through a previously fabricated mask which defines the desired shape of the electrode. Other thin film techniques such as deposition of a metal layer and photo-etching of that layer are also acceptable. The metals used to fabricate the electrodes of the present invention may include one or more of the following: platinum, palladium, rhodium, lead, silver, gold and iridium. It will be understood that other materials may be used as long as they satisfy the requirements of the present invention. These other materials must be capable of promoting a reaction with the species to be detected by the electrochemical sensor, as well as adhering or being adhered to the electrolytic medium. Selection of the proper electrode material for a particular reaction will depend on the species which is to be detected, as well as the ability to adhere the electrode material to the electrolytic medium.

Once electrodes have been deposited on the surface of the layer of electrolytic material, it may be desirable to add a second layer of electrolytic material atop the electrodes to increase the mechanical strength of the sensor, as well as to protect the electrodes. The second layer of electrolyte can also be deposited by spin coating techniques. However, additional problems exist with the use of spin coating over electrodes since the electrolytic material must be deposited on rough, uneven surfaces which are formed by the electrodes. Therefore, the spin speed and the viscosity of electrolyte may have to be adjusted to accomplish the desired coating.

When applying an electrolyte coating over the surface of electrodes it is preferable to reduce the spin speed of the substrate during the spin coating process. This is because centrifugal forces generated during the spin coating process will cause tearing of the electrolyte coating at the edges of the electrodes. However, if the spin speed is reduced, too much wetting of the lower electrolyte layer will produce some strain in the electrode structure. This strain may cause the electrode to distort and lift off the substrate. Therefore the spin speed during the spin coating process must be carefully adjusted to provide an electrolyte coating having the desired properties. Adjustments are made according to the viscosity of the medium and the required step coverage. The step coverage or step height is determined by the thickness of the electrode (or step) that exists on the substrate to be covered. The preferred spin speed for electrolytic coating onto the surface of electrodes is from about 50 r.p.m. to about 1000 r.p.m. More preferably, the spin speed is from about 100 r.p.m. to about 500 r.p.m. and most preferably the spin speed is between about 100 r.p.m. and about 300 r.p.m.

Another way to improve the properties of the electrolyte coating which is applied to the surface of the electrodes is to adjust the viscosity of the coating material. Increasing the viscosity of the electrolytic material will cause a corresponding increase in the thickness of the electrolytic layer coated onto the electrode surface. Decreasing the viscosity will have the corresponding effect of decreasing the film thickness of the electrolytic layer on the electrode surface. As a result, the mechanical and thermal properties of the electrolyte layer can be adjusted by adjusting the viscosity of the coating solution. Perffered viscosities of the coating solution are from about 30 to about 200 centistokes.

The same types of electrolytes may be used to coat over the surface of the electrodes as were used to coat directly onto the substrate. However, electrolytes having a higher viscosity may be desirable for coating over the surface of the electrodes as a result of the necessity of coating an uneven surface.

Referring now to FIG. 1 there is shown an electrochemical sensing apparatus 10 including a substrate 11, an electrolyte 22, a counter electrode means 13 and a working electrode means 14. The sensor depicted in FIG. 1 is the simplest, least expensive and one of the most efficient sensors fabricated in accordance with the present invention.

Figure 2:
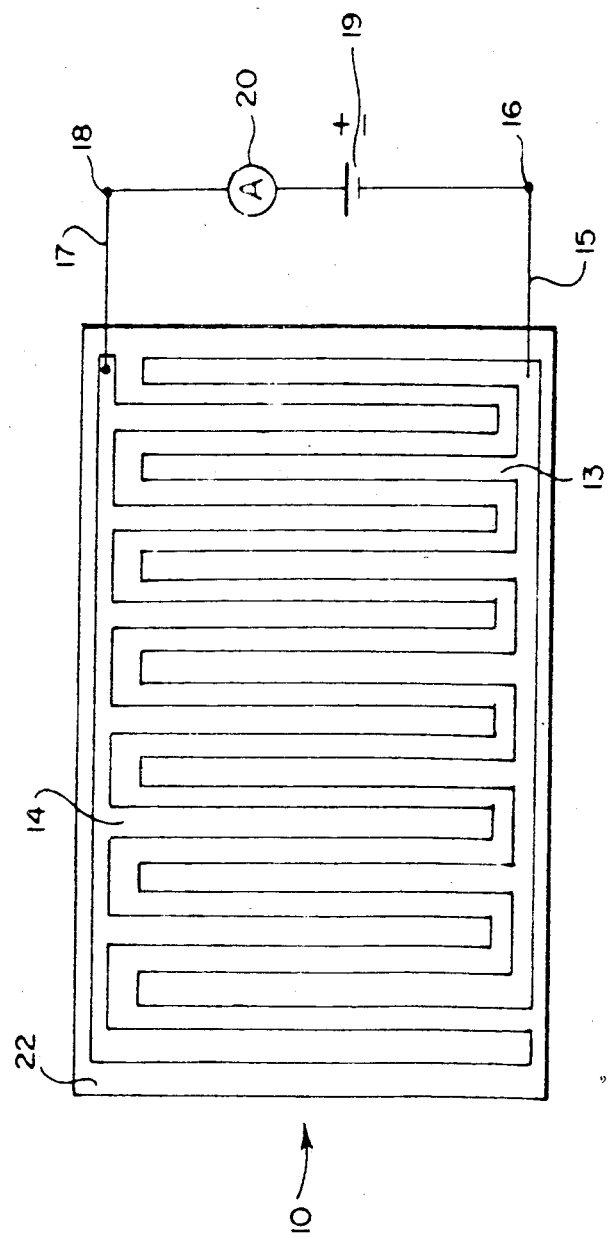
FIG. 2 is a top view of the amperometric electrochemical sensing apparatus of the present invention.

Referring now to FIG. 2 which is a top plan view of the apparatus of FIG. 1 showing the finger-like projections of the electrodes 13 and 14. Counter electrode 13 is connected by way of line 15 to terminal 16 and the working electrode 14 is connected by line 17 to the terminal 18. The electrical circuit also includes a series connected potential source 19 for biasing the working electrode means 14 at a desired potential and an ammeter 20.

Referring now to FIG. 3 there is shown an alternate embodiment of the electrochemical sensor of the present invention. The sensor depicted in FIG. 3 includes substrate 11 having an oxide layer 21 on the surface thereof. Deposited on the oxide layer 21 and adhering to the oxide layer 21 is a first layer 25 of electrolytic medium. Deposited on the first layer 25 of electrolytic medium are the counter electrode means 13 and the working electrode means 14. Also deposited on the first layer 25 of electrolytic medium is a reference electrode 23 having a protective coating 24 thereon. Deposited on top of the electrodes 13, 14 and the protective coating 24 is a second layer 27 of electrolytic medium. Finally, on top of the second layer 27 of electrolytic medium is shown a selectively permeable membrane 26. This selectively permeable membrane 26 serves to allow the diffusion of the species to be detected through to the working electrode 14 and the electrolytic medium. However, it does not allow diffusion of certain other materials which may be present in the fluid material being sensed. Therefore, the membrane 26 can be used to improve species specificity of the sensing apparatus. The membrane 26 can also be used to prevent harmful components of the fluid material being sensed from reaching the electrodes 13, 14 and the electrolytic medium and altering their properties in some way. the membrane 26 may be composed of any material which is selectively permeable to the species being detected. Such materials include rubbers and synthetic polymers among other materials.

Referring now to FIG. 4 there is depicted another alternative embodiment of the present invention wherein the electrochemical sensing means is formed in a sandwich-type structure. This sandwich-type structure is built on a layer of substrate 11. The layer of substrate 11 includes an oxide layer 21 on the surface thereof. Deposited on top of the oxide layer 21 is a first layer 25 of electrolytic medium. Deposited on the first layer 25 of electrolytic medium is the counter electrode means 13 and the reference electrode 23. The reference electrode 23 is coated by a protective coating 24. Depostied on top of the counter electrode 13 and protective coating 24 is a second layer 27 of electrolytic medium. Then, deposited on the second layer 27 of electrolytic medium is the working electrode means 14 of the electrochemical sensor. Deposited on top of the working electrode means 14 is a third layer 28 of electrolytic medium which includes a selectively permeable membrane 26 thereon.

Figure 5:
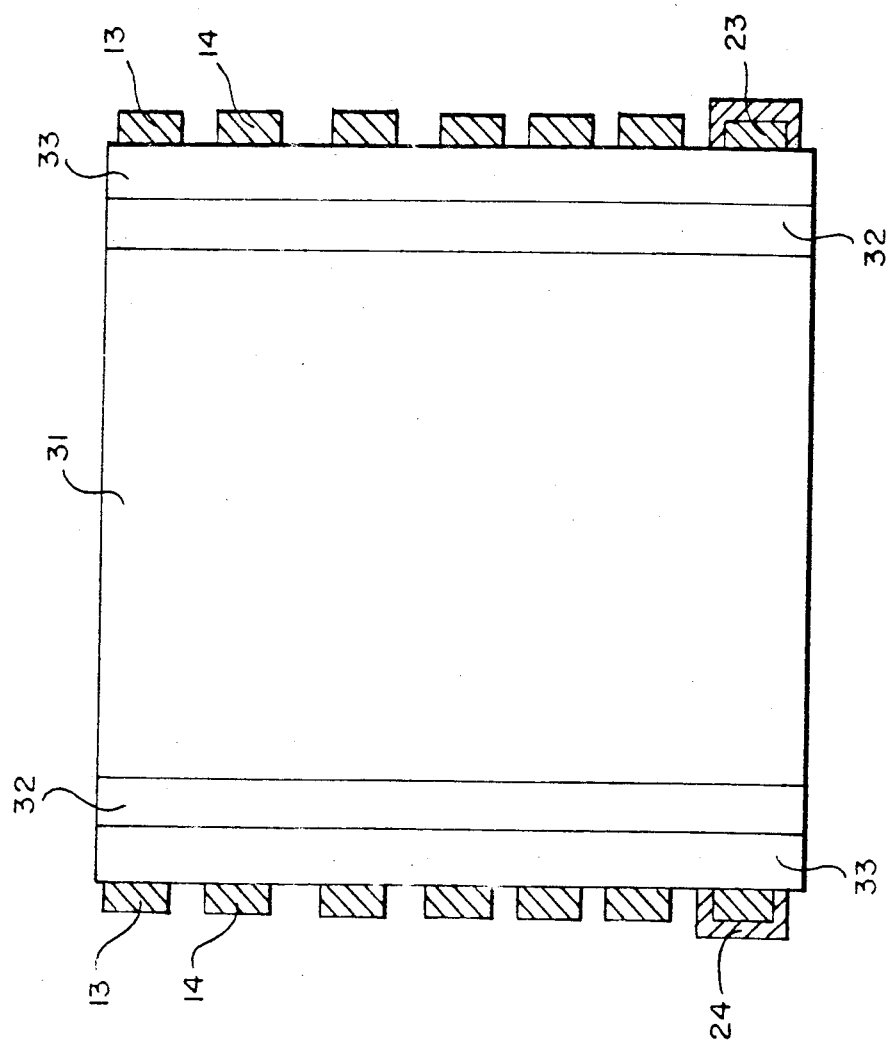
FIG. 5 is a cross-section view of a cylindrical amperometric electrochemical sensing apparatus in accordance with the present invention.

Referring now to FIG. 5 there is shown yet another alternate embodiment of a sensor which may be fabricated in accordance with the present invention. FIG. 5 depicts a cross-sectional view of a cylindrical electrochemical sensor fabricated in accordance with the method of the present invention. The cylindrical electrochemical sensor includes a substrate 31 having an oxide layer 32 on the surface thereof. On top of the oxide layer 32 is deposited a first layer 33 of electrolytic medium. On the first layer 33 of electrolytic medium is deposited a counter electrode means 13, a working electrode means 14 and a reference electrode 23. The reference electrode 23 is coated with a protective coating 24. It will be understood that any of the alternate embodiments shown in FIGS. 1-4 may be adapted to the cylindrical-shaped electrochemical sensor as well as other possible shapes such as spherical. These alternate shapes may be desirable for specific applications of the sensing device.

The following examples are provided to illustrate the present invention.

EXAMPLE 1

A 5% Nafion solution (perfluorinated ion-exchange powder, Aldrich Chemical Co., Milwaukee, Wis.) was spin coated onto a silicon substrate using the method of the present invention. A Nafion solution having a viscosity of 100 centistokes was used and the turntable was rotated at 650 r.p.m. The Nafion formed a smooth, uniform surface on the silicon substrate with no visible pin holes, cracks, or other imperfections. The film of Nafion passed the scotch tape test when dry and was difficult to peel off the substrate. The coating was about ½ micron thick. Heating to 100° C. for several hours did not cause any deterioration of the coating.

Gold films (99.99%, Engelhard Minerals and Chemicals Co., N.J.) were deposited on the spun on Nafion electrolyte. The gold adhered well to the Nafion under both wet and dry conditions. The sheet resistance was about 0.3 ohm/square.

EXAMPLE 2

A 7000 angstrom thick gold film (99.99% Engelhard Minerals and Chemicals Co., N.J.) was deposited on the surface of a silicon wafer spin coated as in Example 1 with a layer of a 5% Nafion solution (perfluorinated ion-exchange powder, Aldrich Chemical Co. Milwaukee, Wis.) having a viscosity of 100 centistokes, using a two-step evaporation procedure. The wafers were oxidized to provide an insulating silicon dioxide surface prior to coating. The evaporated gold film was covered with a photoresist and etched using standard etching procedures, to form an electrode of the desired geometry.

The same 5% Nafion solution was spin coated over the gold electrode at 100 r.p.m. and produced an electrolytic layer having an amount edge tearing within the acceptable range as well as minimal distortion of the gold electrode.

The foregoing description of embodiments of the invention has been presented for purposes of illustration and description. It is not intended to be exhaustive or to limit the invention to the precise forms disclosed, and many modifications and variations will be obvious to one of ordinary skill in the art in light of the above teachings. Accordingly, the scope of the invention is to be defined by the claims appended hereto.

What is claimed is:

1. A method for the production of a structurally stable, solid electrolyte for use in the fabrication of electrochemical sensors comprising the steps of
    spin coating a solution of an ion-conducting material onto the surface of an insulating substrate, the ion-conducting material being of sufficient viscosity to provide a substantially uniform coating of a solid, structurally stable ion-conducting layer on the substrate, and
    drying the spin coated solution of ion-conducting material to form a substantially uniform coating of a solid, structurally stable ion-conducting layer on the substrate.

2. A method in accordance with claim 1 wherein the viscosity of the ion-conducting material is from about 30 to about 400 centistokes.

3. A method in accordance with claim 2 wherein the surface of the insulating substrate comprises a layer of a hydrophilic material thereon.

4. A method in accordance with claim 3 wherein the hydrophilic layer comprises at least one oxide.

5. A method in accordance with claim 4 wherein the oxide comprises silicon dioxide and the substrate comprises silicon.

6. A method in accordance with claim 4 wherein the ion-conducting material is spin coated onto the surface of the substrate at a spin speed of about 50 r.p.m. to about 5000 r.p.m.

7. A method in accordance with claim 3 wherein the ion-conducting material comprises at least one perfluoro linear polymer.

8. A method in accordance with claim 1 wherein the surface of the insulating substrate comprises at least one electrode thereon.

9. A method for the production of an electrochemical sensor comprising the steps of:
    spin coating an ion-conducting material onto the surface of an insulating substrate, the ion-conducting material being of sufficient viscosity to provide a substantially uniform coating of a solid, structurally stable ion-conducting layer on the substrate, depositing a working electrode and at least one other electrode onto the layer of ion-conducting material, and connecting an electrical power source to the working electrode and the at least one other electrode to thereby complete a circuit in which current is capable of flowing through both of the electrodes as a result of at least one electrochemical reaction occurring at the working electrode.

10. A method in accordance with claim 9 wherein the viscosity of the ion-conducting material is from about 30 to about 400 centistokes.

11. A method in accordance with claim 10 wherein the surface of the insulating substrate comprises a layer of a hydrophilic material thereon.

12. A method in accordance with claim 11 wherein the layer of hydrophilic material comprises at least one oxide.

13. A method in accordance with claim 11 wherein the ion-conducting material is spin coated onto the surface of the substrate at a spin speed of about 50 r.p.m. to about 5000 r.p.m.

14. A method in accordance with claim 13 wherein the ion-conducting material comprises at least one perfluoro linear polymer.

15. A method in accordance with claim 9 further comprising the step of:

spin coating an ion-conducting material onto the working electrode and the at least one other electrode, the ion-conducting material being of sufficient viscosity to provide a substantially uniform coating of a solid, structurally stable second ion-conducting layer on the working electrode and the at least one other electrode.

16. A method in accordance with claim 15 wherein the second ion-conducting layer is spin coated onto the working electrode and at least one other electrode at a spin speed of about 50 r.p.m. to about 1000 r.p.m.

17. A method in accordance with claim 16 wherein the ion-conducting material for the second ion-conducting layer has a viscosity of from about 30 to about 400 centistokes.

18. A method for the production of a sandwich-type electrochemical sensor comprising the steps of:

spin coating an ion-conducting material onto the surface of an insulating substrate, the ion-conducting material being of sufficient viscosity to provide a substantially uniform coating of a solid, structurally stable first ion-conducting layer on the substrate, depositing at least one electrode onto the first layer of ion-conducting material, spin coating an ion-conducting material onto the at least one electrode, the ion-conducting material being of sufficient viscosity to provide a substantially uniform coating of a solid, structurally stable second ion-conducting layer on the at least one electrode, depositing a working electrode onto the second layer of ion-conducting material, and connecting an electrical power source to the working electrode and to the at least one other electrode to thereby complete a circuit in which current is capable of flowing through both of the electrodes as a result of at least one electrochemical reaction occurring at the working electrode.

19. A method as claimed in claim 18 wherein the viscosity of the ion-conducting material of the first ion-conducting layer is from about 30 to about 200 centistokes.

20. A method as claimed in claim 19 wherein the viscosity of the ion-conducting material of the second ion-conducting layer is from about 50 to about 400 centistokes.

21. A method as claimed in claim 20 wherein the surface of the insulating substrate comprises a layer of a hydrophilic material thereon.

22. A method as claimed in claim 21 wherein the hydrophilic material comprises at least one oxide.

23. A method as claimed in claim 21 wherein the first layer of ion-conducting material is spin coated onto the surface of the substrate at a spin speed of between about 50 r.p.m. and about 5000 r.p.m.

24. A method as claimed in claim 23 wherein the second layer of ion-conducting material is spin coated onto the at least one electrode at a spin speed of about 50 r.p.m. to about 5000 r.p.m.

25. A method as claimed in claim 24 wherein the first and second layers of ion-conducting material comprise at least one perfluoro linear polymer.

26. A method as claimed in claim 18 further comprising the step of:

spin coating an ion-conducting material onto the working electrode, the ion-conducting material being of sufficient viscosity to provide a substantially uniform coating of a solid, structurally stable third ion-conducting layer on the working electrode.

* * * * *